United States Patent [19]

Schmitt

[11] Patent Number: 4,487,702

[45] Date of Patent: Dec. 11, 1984

[54] SUBSTITUTED HETEROCYCLIC METHANE SULFONATES AS SACRIFICIAL AGENTS IN ENHANCED OIL RECOVERY

[75] Inventor: Kirk D. Schmitt, Pennington, N.J.

[73] Assignee: Mobil Oil Corporation, New York, N.Y.

[21] Appl. No.: 373,552

[22] Filed: Apr. 30, 1982

[51] Int. Cl.³ .............................................. E21B 43/22
[52] U.S. Cl. .............................. 252/8.55 D; 166/274; 166/275
[58] Field of Search .................. 252/8.55 D; 166/274, 166/275

[56] References Cited

U.S. PATENT DOCUMENTS 3,469,630  9/1969  Hurd et al. ........................... 166/350
3,875,187  4/1975  Hickner et al. ............... 204/158 NE
4,172,498  10/1979  Kalfoglou ...................... 252/8.55 D
4,410,709  10/1983  Ohme et al. ......................... 548/570

OTHER PUBLICATIONS

Chemical Abstracts, vol. 96, No. 219688, 1982.

Primary Examiner—Christine M. Nucker
Attorney, Agent, or Firm—Alexander J. McKillop; Michael G. Gilman; Stanislaus Aksman

[57] ABSTRACT

There is provided a sacrificial agent for enhanced oil recovery which is a 5-membered heterocyclic ring having a methane sulfonate group substituted at the 3-position and a methyl group substituted in the 4-position. Methods of using these sacrificial agents are also provided.

17 Claims, 2 Drawing Figures

SUBSTITUTED HETEROCYCLIC METHANE SULFONATES AS SACRIFICIAL AGENTS IN ENHANCED OIL RECOVERY

BACKGROUND OF THE INVENTION

Field of the Invention

This invention is directed to substituted heterocyclic methane sulfonates as sacrificial agents in enhanced oil recovery.

In the recovery of oil from oil-bearing subterranean reservoirs, it usually is possible to recover only minor portions of the original oil in place by the so-called primary recovery methods which utilize only the natural forces in the reservoir. In order to increase the production of oil from subterranean reservoirs, resort has been taken to a variety of supplemental (secondary) recovery techniques. The most widely used supplemental technique is waterflooding, which involves the injection of water into the reservoir. As the water moves through the reservoir, it acts to displace oil therein toward a production system comprising one or more wells through which the oil is recovered.

It has long been recognized that factors such as the interfacial tension between the injected water and the reservoir oil, the relative mobilities of the reservoir oil and injected water, and the wettability characteristics of the rock surfaces within the reservoir are factors which influence the amount of oil recovered by waterflooding. Thus, it has been proposed to add surfactants to the flood water in order to lower the oil-water interfacial tension and/or to alter the wettability characteristics of the reservoir rock. Also, it has been proposed to add viscosifiers such as polymeric thickening agents to all or part of the injected water in order to increase the viscosity thereof, thus decreasing the mobility ratio between the injected water and oil and improving the sweep efficiency of the waterflood.

Surfactants used for enhanced oil recovery, particularly brine tolerant surfactants, are very expensive. Such surfactants tend to be absorbed by the rocks and clays in the reservoir, thus depleting their concentration in the waterflood fluid and diminishing their effectiveness by unfavorably increasing oil-water interfacial tension. A way to reduce absorptive loss is to use cheaper chemicals, i.e., sacrificial agents, that are absorbed on the rock, leaving the surfactants relatively less absorbed and free for its intended purpose.

The addition of various compounds to enhanced oil recovery fluids to reduce absorptive loss of surfactants to rock is not a new concept. Compounds which have been found to be effective include sodium phosphates (Roszelle U.S. Pat. No. 3,688,844), sodium silicates [P. Somasundaran and H. S. Hanna, *Society of Petroleum Engineers*, paper 7059 (1978] and lignosulfonates [Kalfoglou U.S. Pat. No. 4,000,779 and Anon., *Paper Trade Journal*, 163, 21 (1979)]. These compounds were selected for their cheapness and effectiveness. However, it has been found that certain low molecular weight heterocyclic methanesulfonates of the present invention are even more effective than the most effective of the above named compounds, namely, the lignosulfonates.

SUMMARY

The present invention provides sacrificial agents of the formula

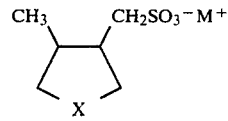

where:
(i) X is selected from the group consisting of O, S,

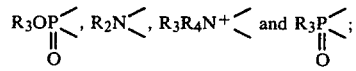

(ii) M is selected from the group Na, K, Li and $NH_4$; and
(iii) $R_2$ is selected from the group consisting of hydrogen, methyl, ethyl, n-propyl and i-propyl; and
(iv) $R_3$ and $R_4$ are the same or different and are selected from the group consisting of methyl, ethyl, n-propyl, and i-propyl, provided that M may be absent when X is $R_3R_4N^+$.

The present invention also provides methods of using these sacrificial agents.

DESCRIPTION OF SPECIFIC EMBODIMENTS

Figure 1:
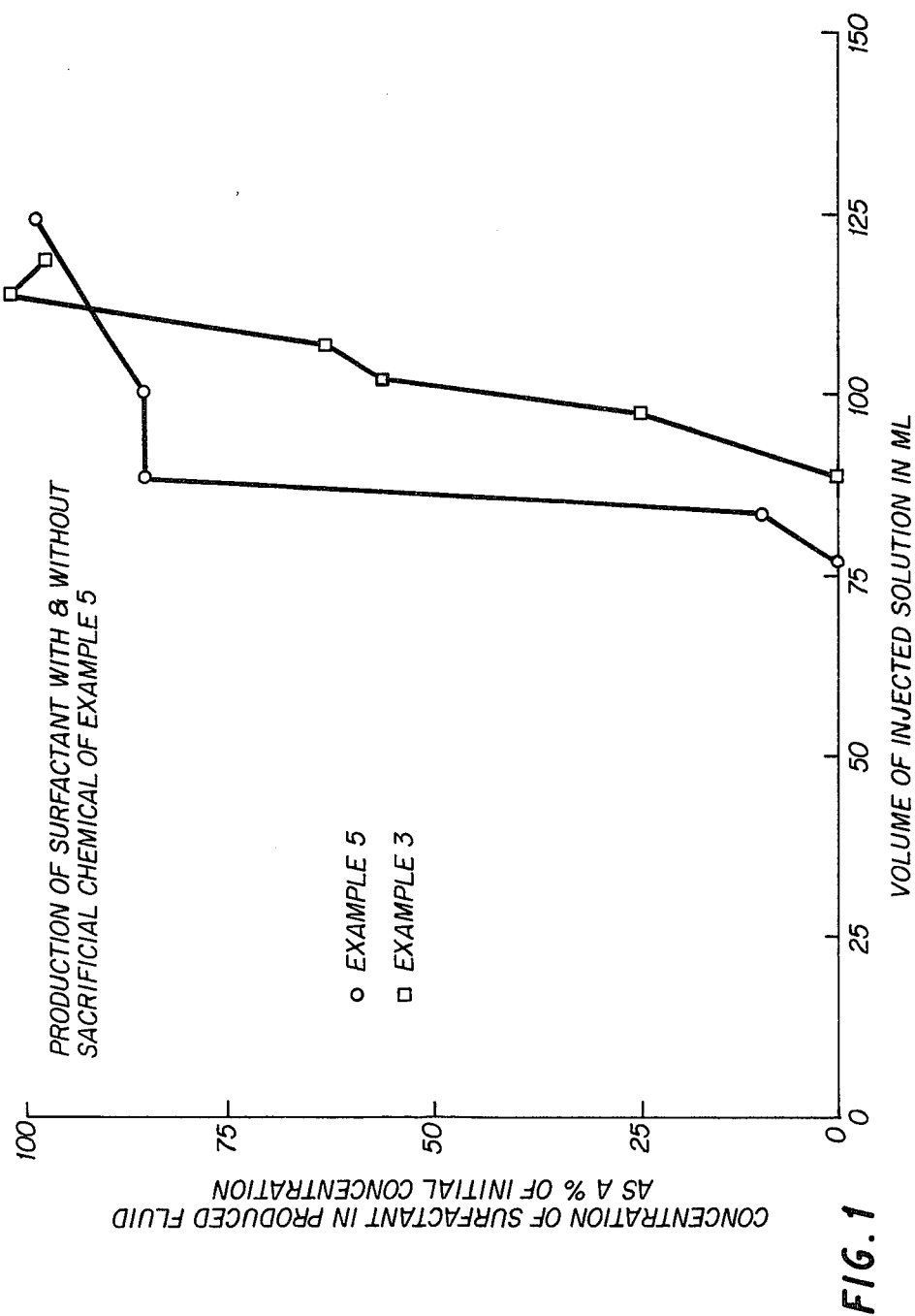
FIG. 1 presents the graphical relationship between the volume of surfactant solution injected with and without sacrificial agent and the concentration of surfactant in produced fluid in percent of initial concentration.

The reaction of olefins with alkali metal bisulfite, in which the bisulfite adds across the double bond, is known. [M. S. Kharasch, E. M. May, F. R. Mayo, J. Org. Chem., 3, 175 (1938)]. The use of cosolvents [Norton et al, U.S. Pat. No. 3,522,297] and initiators [C. F. Norton, N. F. Seppi, and M. J. Reuter, J. Org. Chem., 33, 4158 (1968)] to promote this reaction is also known as is the use of a certain amount of final sulfonate product as solubilizer in those cases where the olefin is not water soluble [Chen et al U.S. Pat. No. 4,267,123].

It has been discovered, quite unexpectedly, that the course of the reaction is different when two double bonds are present in the same molecule in the relationship $X(CH_2CH=CHR)_2$, where X is as defined herein. By way of illustration, it is known that allyl alcohol produces sodium 3-hydroxypropane sulfonate in high yield when treated with sodium bisulfite, air, and water. [R. F. Fischer, Ind. and Eng. Chem., 56, 41 (1964)]. This reaction is illustrated as follows.

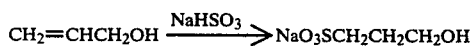

It would be expected that similar treatment of diallyl ether with two or more moles of bisulfite would lead to a disulfonate ether product as follows.

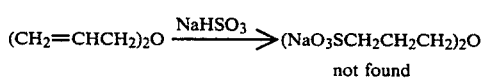

not found

Instead, however, there is produced the unexpected tetrahydrofuran derivative as follows.

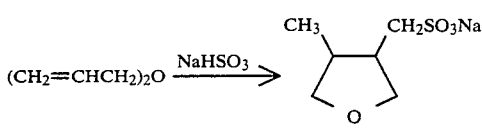

The compounds of this invention are readily prepared by reacting a bisulfite salt and air or oxygen with a diallyl compound, having the formula $X(CH_2CH=CHR)_2$, in an aqueous phase. The reaction proceeds generally at ambient conditions of temperature and pressure, although higher temperatures and pressures may be used if desired. The reaction is carried out in a homogenous aqueous phase. This phase can be water alone, if the olefinic reactant is water soluble. If not, this phase will be a mixture of water and sufficient cosolvent, such as $C_1$-$C_4$ alkanol to dissolve the olefinic reactant.

The bisulfite salt reactant may be any such reactable bisulfite salt such as sodium bisulfite, lithium bisulfite, potassium bisulfite, and ammonium bisulfite. This bisulfite salt may, thus, have the formula $MHSO_3$, where M is Na, Li, K or ammonium.

An oxygen containing gas acts as an initiator. It can be oxygen or air or other molecular oxygen containing gas.

The organic compound starting reactant for preparing the compounds of this invention has the structure, $X(CH_2CH=CH_2)_2$, wherein X and $R_1$ are as defined as herein.

Where X is $R_3R_4N^+$, if $R_3=R_4=R_4=H$, the reactant is commercially available diallyl amine. Compounds where $R_3$ and $R_4$ may not both be H can be prepared by appropriate alkylation reactions, e.g.,

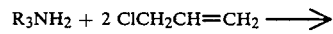

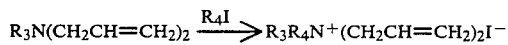

Compounds in which X=O or S are readily available diallyl ether and diallyl thioether. Other ethers are available by the reaction:

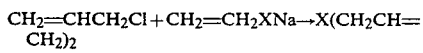

in which X=O or S. $CH_2=CHCH_2XH$ is easily made by reacting $CH_2=CHCH_2Cl$ with aqueous NaOH or KOH.

When

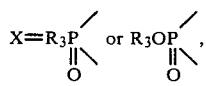

the reactant can be made as follows:

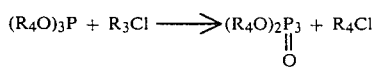

-continued
Arbusov Reaction

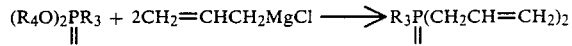

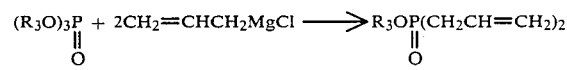

(I. O. Sutherland, "Comprehensive Organic Chemistry", Volume 2, Pergamon Press, Oxford, England, 1979, page 1177).

The following examples illustrate the conditions which give rise to compounds of this invention with a number of different "X" substitutions.

EXAMPLE 1

A solution of 31.9 g. of $NaHSO_3$ in 170 ml. $H_2O$ was added dropwise over 15 min. to a room temperature solution containing 15 g. diallyl ether, 150 ml. $H_2O$, and 150 ml. ethanol while air was bubbled through at about 15 ml./min. An exothermic reaction took the temperature to 40° C. The mixture was evaporated to dryness, extracted with ethanol in a Soxhlet extractor and the ethanol soluble material recrystallized from methanol to give 21.7 g. (72%) white crystals whose elemental analysis was consistent with a mixture of cis and trans isomers of the formula:

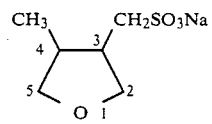

where the cis and trans configuration is with respect to the bond between the 3 and 4 carbon atoms. The theoretical elemental analysis for $C_6H_{11}NaO_4S$ is as follows: C,35.63%; H,5.48%; Na,11.37%; S,15.86%. The following was actually found: C,35.51%; H,5.41%; Na,11.47%; S,15.89%.

The Carbon-13 NMR showed two isomers in ratio 3:1 of six carbons each. The chemical shifts were consistent with cis and trans tetrahydrofurans derivatives of the above formula. The proton multiplicities indicated by the single frequency off resonance decoupled spectrum indicated that each carbon had the correct number of protons for the structures drawn.

| | Carbon 13-NMR Data | | | |
|---|---|---|---|---|
| | cis-isomer | | trans-isomer | |
| Carbon | Shift* | Multiplicity | Shift* | Multiplicity |
| $CH_3$ | 12.3 | q | 14.8 | q |
| $CH_2SO_3$ | 49.2 | t | 52.7 | t |
| 1 | 70.3 | t | 72.4 | t |
| 2,3 | 37.6, 35.1 | d,d | 42.1, 38.6 | d,d |
| 4 | 74.2 | t | 73.6 | t |

*Relative to $(CH_3)_3SiCH_2CH_2CH_2SO_3Na$ as O.

The major isomer was assigned the cis structure because of the relative upfield shifts of its —$CH_2SO_3$ and $CH_3$— carbons. Substituents located cis nearly always show carbon NMR shifts upfield of trans substituents in olefins, cyclohexanes, and cyclopentanes.

[R. A. Friedel and H. L. Retcotsky, J. Amer. Chem. Soc., 85, 1300 (1963); D. K. Dalling and D. M. Grant, ibid, 89,6612 (1967); and M. Chrisrl, H. J. Reich, and J. D. Roberts, ibid, 93, 3463, (1971).]

EXAMPLE 2

A mixture of 15 g. diallylamine, 150 ml. water and 150 ml. t-butyl alcohol at 4° C. was treated with 16.1 g. NaHSO$_3$ and 1 g. Na$_2$SO$_3$ as in Example 1. After 30 minutes the inorganic salts were filtered off and the reaction mixture stripped to give 30.5 g. (98%) of a white solid whose C-13 NMR showed it to be a 9:1 mixture of cis-and trans pyrrolidines of the formula

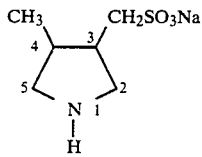

where the cis and trans configuration is with respect to the bond between the 3 and 4 carbon atoms.

| | Carbon 13-NMR Data | | | |
|---|---|---|---|---|
| | cis-isomer | | trans-isomer | |
| Carbon | Shift* | Multiplicity | Shift* | Multiplicity |
| CH$_3$ | 13.0 | q | 14.9 | q |
| CH$_2$SO$_3$ | 48.2 | t | 53.3,50.8 | t |
| 1,4 | 52.2,50.3 | t,t | 51.7 | t,t |
| 2,3 | 38.0,35.3 | d,d | 41.9,38.3 | d,d |

*Relative to (CH$_3$)$_3$SiCH$_2$CH$_2$CH$_2$SO$_3$Na as O.

The major isomer is, assigned the cis configuration because of the relative upfield positions of its CH$_3$ and —CH$_2$SO$_3^-$ resonances.

The method of this invention pertaining to sacrificial agents is applicable as an adjuvant to waterflood operations. It is primarily adapted to secondary recovery of light oils by waterflooding, but could be useful as a supplement to thermal recovery, such as by fireflooding, of heavy oils.

The method is carried out in a subterranean reservoir that is penetrated by spaced apart injection and production systems extending from the surface of the earth into the oil-bearing formation. The injection systems comprises one or more wells into which are introduced fluids. The production system comprises one or more wells from which product is recovered. The wells in the injection and production systems are spaced apart and can be arranged in any desired pattern, such pattern being well known in waterflood operations. For example, the pattern can comprise a central injection well and a plurality of recovery wells spaced radially about the injection well.

The aqueous fluid used in the method of this invention pertaining to sacrificial agents is water or brine. An ideal source of brine is connate water previously obtained in production from the formation. The aqueous fluid may contain surfactants, such as anionic surface active agents, and may contain viscosifiers, such as polymeric thickening agents. Where brine is used as the aqueous fluid, the brine may have salinity of at least 5% by weight and/or a divalent ion concentration of from about 200 to about 20,000 ppm.

Any surfactant known in the art which will lower the interfacial tension between the injected aqueous solution and the reservoir oil can be used. More generally used are anionic alkali metal or ammonium surfactants. Typical surfactants include petroleum sulfonates, alkyl-phenoxypoly(ethyleneoxy)propane sulfonates, and alkoxypoly(ethyleneoxy)propane sulfonates. Ordinarily the concentration of surfactant used will be between about 0.01 percent and about one percent. The alkoxy- or alkylphenoxypolyethlyeneoxypropane sulfonates will generally have 8–30 carbon atoms in the alkyl group, straight chain or branched, and 3–6 ethyleneoxy groups.

The addition of from about 0.3 to about 6% by weight of the sacrificial agents of the present invention, based upon the weight of the entire fluid to enhanced oil recovery fluids not only reduces adsorptive loss but causes oil to be produced by such fluids at an earlier stage in the injection thus reducing the cost of the process.

Surfactants for enhanced oil recovery and, in particular, brine tolerant surfactants are an expensive part of any enhanced oil recovery fluid. Consequently any inexpensive chemical which can reduce the amount of surfactant required can reduce the cost of the fluid. Since substantial amounts of time are required between the time an enhanced oil recovery fluid is injected and the time oil is produced a chemical which forces earlier production of oil can reduce costs simply by reducing the cost of borrowed money.

To illustrate the efficiency of sacrifical agents according to the present invention, three oil recovery experiments were carried out. In each case a six foot long glass column was packed with 160 g Berea sand, evacuated, filled with brine, the brine displaced with crude oil until no more oil was produced, then the oil displaced by brine until no more oil was produced. All solutions were flowed at 1.5 ml/hr. The brine contained 16.6% solids with the following composition:
NaCl=13.2%
MgCl$_2$=0.72%
CaCl$_2$=2.62%

In each experiment a surfactant solution consisting of 0.525% sulfonate A and 0.175% alcohol B was injected continuously.

A
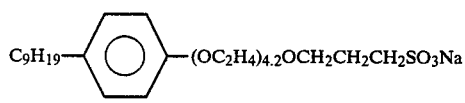

B
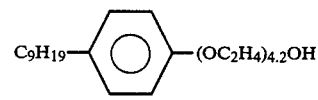

The amount of oil produced was determined volumetrically and the concentration of the surfactant A was determined by injecting produced aqueous solutions onto a Whatman ODS high pressure liquid chromatographic (HPLC) column. The effluent from the HPLC column was analyzed at 280 nm while the composition of the eluting solvent was varied linearly from 1.5 ml/min H$_2$O to 1.5 ml/min CH$_3$OH. The surfactant B had an elution time of 9.4 minutes.

In each case the weight of surfactant absorbed was determined by comparison of the concentration of surfactant produced to the concentration expected under conditions of plug flow and no absorption. The results of these experiments are set forth in Examples 3–6 as follows.

EXAMPLE 3

Figure 2:
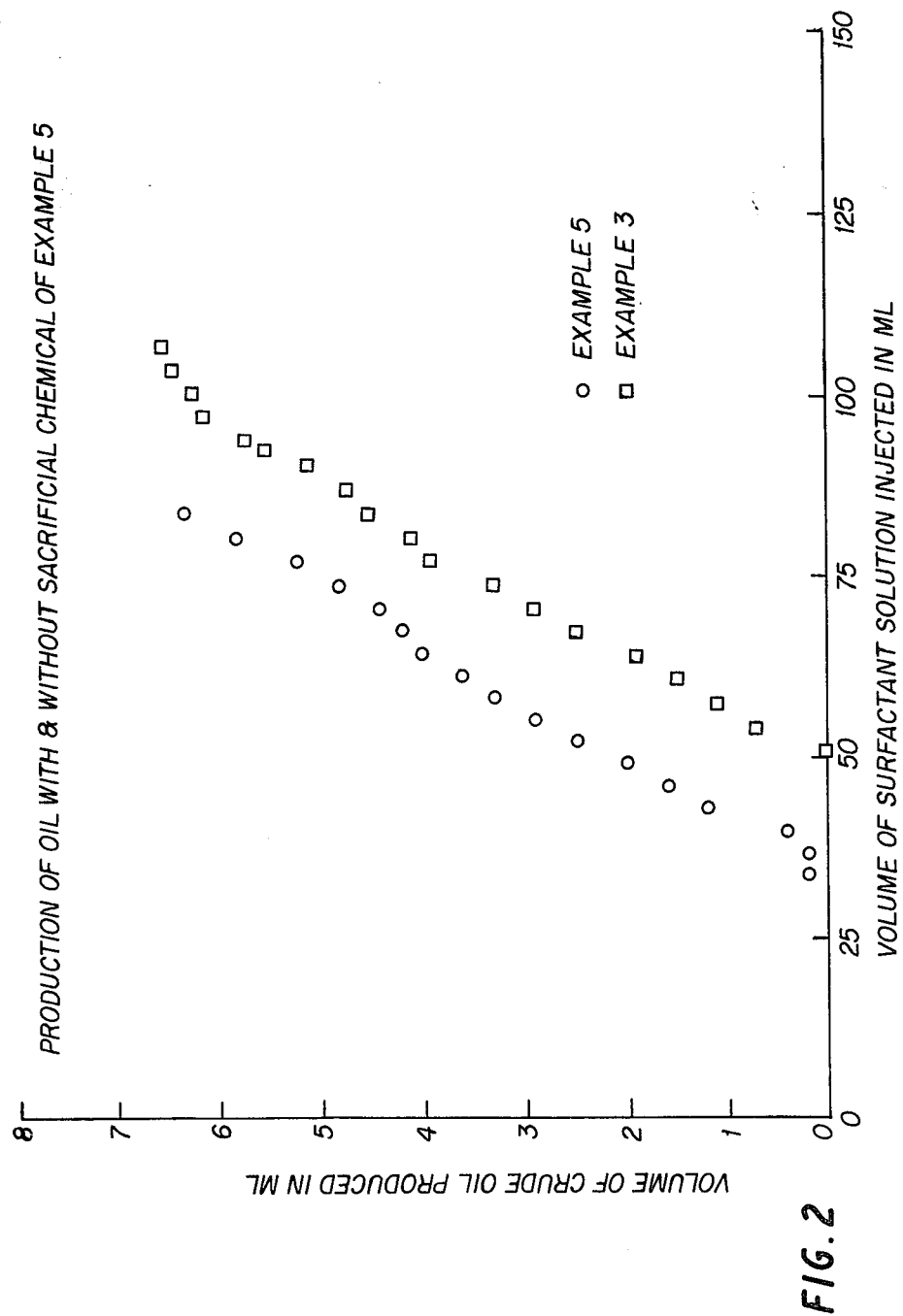
FIG. 2 presents the graphical representation between the volume of surfactant injected with and without sacrificial agent and the volume of oil produced.

A control experiment was carried out as described above with no added sacrificial agents. The amount of surfactant absorbed was determined to be 450 mg. The production profiles for oil and surfactant in this experiment are shown in FIGS. 1 and 2.

EXAMPLE 4

An oil recovery experiment was carried out as described above but 3% ERA-4, a lignosulfonate from American Can Corporation, was added to the surfactant solution as a sacrificial chemical. The amount of surfactant absorbed was determined to be 365 mg, a reduction of 19%.

EXAMPLE 5

An oil recovery experiment was carried out as described above but 3% of a compound of the formula

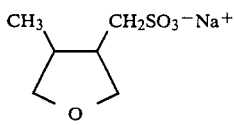

was added to the surfactant solution as a sacrificial chemical. The amount of surfactant absorbed was determined to be 280 mg, a reduction of 38% over the control. The production profiles for oil and surfactant are also shown in FIGS. 1 and 2 and they show quite clearly that the additive caused both reduced absorption and earlier oil production.

EXAMPLE 6

An oil recovery experiment was carried out as described above but 3% sodium 3-hydroxypropanesulfonate was added to the surfactant solution as a sacrificial chemical. The amount of surfactant absorbed was determined to be 410 mg, within experimental error of the control.

The patents and literature articles cited herein are hereby expressly incorporated herein by reference.

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. A method for the recovery of oil from a subterranean oil reservoir penetrated by spaced apart injection system and production system in which an aqueous surfactant fluid is injected into the reservoir via the injection system to displace oil to the production system, said method comprising injecting into said reservoir an aqueous fluid comprising dissolved sacrificial agent in an amount sufficient to decrease the retention of surfactant in said reservoir, said sacrificial agent being a compound according to the formula

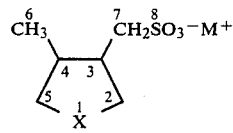

where:
(i) X is selected from the group consisting of O, S,

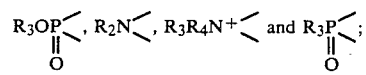

(ii) M is selected from the group consisting of Na, K, Li and NH$_4$; and
(iii) R$_2$ is selected from the group consisting of hydrogen, methyl, ethyl, n-propyl and i-propyl; and
(iv) R$_3$ and R$_4$ are the same or different and are selected from the group consisting of methyl, ethyl, n-propyl, and i-propyl, provided that M is absent when X is R$_3$R$_4$N$^+$.

2. A method according to claim 1, wherein X is O and M is Na.

3. A method according to claim 1, wherein X is NH and M is Na.

4. A method according to any one of claims 1, 2 and 3, wherein said sacrificial agent constitutes from about 0.3 to about 6% by weight of said injected fluid.

5. A method according to claim 1 wherein X is O.

6. A method according to claim 1 wherein X is R$_2$N> or R$_3$R$_4$N$^+$>.

7. A method according to claim 5 wherein said sacrificial agent constitutes from about 0.3 to about 6% by weight of said injected fluid.

8. A method according to claim 6 wherein said sacrificial agent constitutes from about 0.3 to about 6% by weight of said injected fluid.

9. A method according to claim 4 wherein said aqueous fluid also comprises a surfactant.

10. A method according to claim 9 wherein the surfactant is selected from the group consisting of anionic alkali metals, ammoniun sulfonates, petroleum sulfonates, alkylphenoxypoly(ethyleneoxy)propane sulfonates and alkoxypoly(ethyleneoxy)propane sulfonates.

11. A method according to claim 10 wherein the surfactant is present in the amount of about 0.01% to about 1%.

12. A method according to claim 7 wherein said aqueous fluid also comprises a surfactant.

13. A method according to claim 12 wherein the surfactant is selected from the group consisting of anionic alkali metals, ammonium sulfonates, petroleum sulfonates, alkylphenoxypoly(ethyleneoxy)propane sulfonates and alkoxypoly(ethyleneoxy)propane sulfonates.

14. A method according to claim 13 wherein the surfactant is present in the amount of about 0.01% to about 1%.

15. A method according to claim 8 wherein said aqueous fluid also comprises a surfactant.

16. A method according to claim 15 wherein the surfactant is selected from the group consisting of anionic alkali metals, ammonium sulfonates, petroleum sulfonates, alkylphenoxypoly(ethyleneoxy)propane sulfonates and alkoxypoly(ethyleneoxy)propane sulfonates.

17. A method according to claim 16 wherein the surfactant is present in the amount of about 0.01% to about 1%.

* * * * *

UNITED STATES PATENT AND TRADEMARK OFFICE
CERTIFICATE OF CORRECTION

PATENT NO. : 4,487,702

DATED : December 11, 1984

INVENTOR(S) : KIRK D. SCHMITT

It is certified that error appears in the above-identified patent and that said Letters Patent is hereby corrected as shown below:

Column 3, line 65: in the formula "$(R_4O)_3P + R_3Cl \longrightarrow (R_4O)_2P_3 + R_4Cl$"
$$\overset{\|}{O}$$

should be --$(R_4O)_3P + R_3Cl \longrightarrow (R_4O)_2PR_3 + R_4Cl$--.
$$\overset{\|}{O}$$

Column 8, line 31:

"$R_2N >$ or $R_3R_4N+ > .$" should be --$R_2N <$ or $R_3R_4N+ < .$--.

Signed and Sealed this

*Thirtieth* Day of *April 1985*

[SEAL]

Attest:

DONALD J. QUIGG

*Attesting Officer*  *Acting Commissioner of Patents and Trademarks*